United States Patent [19]

Robertson

[11] Patent Number: 4,515,796

[45] Date of Patent: May 7, 1985

[54] CERTAIN NAPHTHALENYL IMIDAZO COMPOUNDS AND THEIR PHARMACEUTICAL USE

[75] Inventor: David W. Robertson, Indianapolis, Ind.

[73] Assignee: Eli Lilly and Company, Indianapolis, Ind.

[21] Appl. No.: 530,315

[22] Filed: Sep. 8, 1983

[51] Int. Cl.$^3$ ............... A61K 31/435; A61K 31/52; C07D 471/04; C07D 473/00
[52] U.S. Cl. .................................. 514/303; 514/261; 544/264; 544/277; 546/118
[58] Field of Search ............... 546/118; 544/264, 277; 424/253, 256

[56] References Cited

U.S. PATENT DOCUMENTS

| 3,985,891 | 10/1976 | Kutter et al. | 424/263 |
| 4,299,834 | 11/1981 | Austel et al. | 424/253 |
| 4,327,100 | 6/1980 | Austel et al. | 424/256 |
| 4,336,257 | 6/1982 | Baldwin | 424/256 |

FOREIGN PATENT DOCUMENTS 820316 8/1969 Canada ................ 260/239.04
72926 3/1983 European Pat. Off. .
79083 5/1983 European Pat. Off. .

OTHER PUBLICATIONS

Chemical Abstracts 88:22904s (1978), abstracting Russian Patent USSR 566,842.
Chemical Abstracts 78:16096g (1973) abstracting Serbian publication *Glas. Hem. Drus., Beograd,* 36(3-4), 137(1971).
*Journal of Heterocyclic Chemistry,* 4, 483(1967) Francis H. Case and Lloyd Kennon.

*Primary Examiner*—Henry R. Jiles
*Assistant Examiner*—Bernard I. Dentz
*Attorney, Agent, or Firm*—Leroy Whitaker; Arthur R. Whale

[57] ABSTRACT

This invention provides for certain naphthalenylimidazo compounds, their pharmaceutical formulations, and their use as positive inotropic agents, bronchodilators, vasodilators, and anticoagulants.

20 Claims, No Drawings

CERTAIN NAPHTHALENYL IMIDAZO COMPOUNDS AND THEIR PHARMACEUTICAL USE

BACKGROUND OF THE INVENTION

The cardiac glycosides and the sympathomimetic amines are the principal inotropic agents used in the management of congestive heart failure. Although the cardiac glycosides, especially digitalis, are among the most frequently prescribed drugs, they have numerous liabilities such as a low therapeutic index and erratic absorption, and are associated with life-threatening arrhythmias and deleterious drug-drug interactions. In addition, many patients either do not respond, or become refractory to these agents. The sympathomimetic amines, such as dopamine and epinephrine, have limited utility due to positive chronotropic effects, arrhythmogenic properties, and oral ineffectiveness.

More recently, new classes of inotropic agents have been found. Among these, certain 2-phenylimidazo[4,5-b]pyridines (U.S. Pat. Nos. 3,985,891 and 4,327,100) have been shown to possess inotropic and anticoagulant activity. U.S. Pat. No. 4,299,834, German Offenlegungsschrift DE No. 3,044,497, and European patent application No. 49,407 describe similarly substituted purine and 6-hydroxy-imidazo[4,5-b]pyridine derivatives. The analogous imidazo[4,5-c]pyridines have also been taught to possess inotropic activity; see European patent application Nos. 72,926 and 79,083.

The present invention provides for a series of naphthalenylimidazo derivatives, their pharmaceutical formulations, and their use as orally effective positive inotropic agents which have minimal effects on blood pressure and heart rate. The compounds also possess vasodilatory, bronchodilatory, and anticoagulant activities.

SUMMARY OF THE INVENTION

This invention provides for pharmaceutically useful imidazo compounds having the formulae

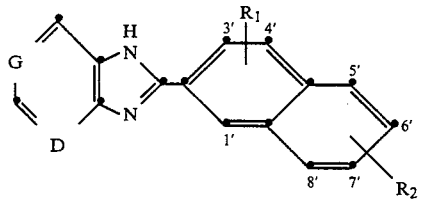

and

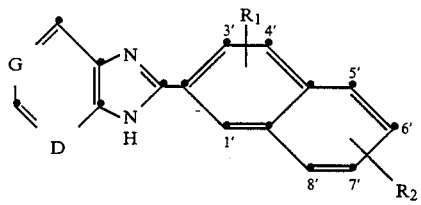

and their pharmaceutically acceptable salts, wherein:
each of $R_1$ and $R_2$ is independently hydrogen, $C_1-C_4$ alkyl, $C_1-C_4$ alkoxy, allyloxy, propargyloxy, benzyloxy, ($C_1-C_4$ alkyl)thio, ($C_1-C_4$ alkyl)sulfinyl, ($C_1-C_4$ alkyl)sulfonyl, hydroxy, halo, cyano, nitro, amino, mono- or di-($C_1-C_4$ alkyl)amino, trifluoromethyl, or Z-Q-substituted $C_1-C_4$ alkoxy, wherein Q is oxygen, sulfur, sulfinyl, sulfonyl, or a bond, and Z is $C_1-C_4$ alkyl, phenyl or phenyl substituted with halo, $C_1-C_4$ alkyl, $C_1-C_4$ alkoxy, hydroxy, nitro, amino, ($C_1-C_4$ alkyl)thio, ($C_1-C_4$ alkyl)sulfinyl, or ($C_1-C_4$ alkyl)sulfonyl; and
G and D are each independently N or CH with the proviso that G and D may not both be CH at the same time.

In addition, this invention also provides a method of treating a warm-blooded mammal, including a human, suffering from or susceptible to the conditions of asthma, thrombosis, hypertension, or heart failure, which comprises administering to said mammal an effective amount of a compound of formula I or Ia.

According to a further aspect of the present invention there is provided a pharmaceutical formulation which comprises as active ingredient a compound of Formula I or Ia as defined above, associated with a pharmaceutically acceptable carrier therefor.

DETAILED DESCRIPTION AND PREFERRED EMBODIMENT

The Formulae I and Ia are recognized as being tautomeric structures of one another. The imidazo compounds having the hydrogen atom on one of the imidazo nitrogen atoms (e.g., Formula I) have corresponding tautomeric forms wherein the hydrogen atom is on the other imidazo nitrogen atom (e.g., Formula Ia). As N-unsubstituted compounds, each tautomeric form exists in equilibrium with the other and cannot be prepared or isolated without the presence of the other. For this application, both forms will be considered together. Thus, the compounds of Formula I (Ia) where G is CH and D is N are known as 2-(2-naphthalenyl)-1H(or 3H)-imidazo[4,5-b]pyridines; where G is N and D is CH, the compounds are 2-(2-naphthalenyl)-1H(or 3H)-imidazo[4,5-c]pyridines; and when G and D are both N, the compounds are 8-(2-naphthalenyl)-7H(or 9H)-purines. For simplicity, these compounds will be referred to as compounds of Formula I (Ia) or by name without designating on which nitrogen atom the hydrogen atom is found.

A preferred group of compounds are the compounds of Formula I (Ia) wherein each of $R_1$ and $R_2$ is independently hydrogen, $C_1-C_4$ alkyl, $C_1-C_4$ alkoxy, halogen, ($C_1-C_4$ alkyl)thio, ($C_1-C_4$ alkyl)sulfinyl, ($C_1-C_4$ alkyl)sulfonyl, or Z-Q-substituted $C_1-C_4$ alkoxy; and pharmaceutically acceptable salts thereof.

Especially preferred compounds as defined above are those where "$C_1-C_4$ alkyl" is methyl, "($C_1-C_4$ alkyl)sulfinyl" is methyl sulfinyl, "($C_1-C_4$ alkyl)sulfonyl" is methyl sulfonyl, and "$C_1-C_4$ alkoxy" is methoxy. Preferred Z-Q-substituted $C_1-C_4$ alkoxy commethoxy. compounds are those wherein $C_1-C_4$ alkoxy is ethoxy or n-propoxy, Q is oxygen, sulfur or sulfinyl, and Z is $C_1-C_4$ alkyl, phenyl or phenyl substituted with halo, $C_1-C_4$ alkoxy, or hydroxy. Compounds substituted at the 1' or 3' position with hydrogen or $C_1-C_4$ alkoxy, especially methoxy, and at the 6'-position with hydrogen, $C_1-C_4$ alkoxy, ($C_1-C_4$ alkyl)sulfinyl, or ($C_1-C_4$ alkyl)sulfonyl are particularly preferred.

Also preferred are those compounds wherein G is N and D is CH, i.e., the 2-(2-naphthalenyl)imidazo[4,5-c]pyridines.

The following definitions refer to the various terms used throughout this disclosure.

The term "halo" refers to fluoro, chloro, bromo, and iodo.

The term "$C_1$-$C_4$ alkyl" refers to the straight and branched aliphatic radicals of one to four carbon atoms including methyl, ethyl, propyl, isopropyl, butyl, isobutyl, sec-butyl, and tert-butyl.

The term "$C_1$-$C_4$ alkoxy" includes the straight and branched aliphatic ether radicals of one to four carbon atoms such as methoxy, ethoxy, propoxy, isopropoxy, butoxy, isobutoxy, sec-butoxy, and tert-butoxy.

The compounds of this invention as represented by Formulas I and Ia may be prepared by any of several methods known in the art.

A preferred method of preparation consists of the reaction of an amine of the formula

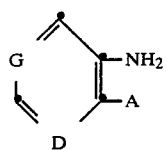

III wherein A is amino, with a compound of the formula

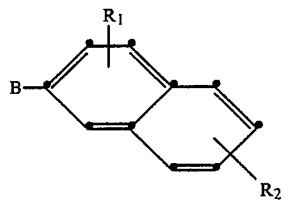

IV wherein B is —COOH, and $R_1$ and $R_2$ are as defined above. The reaction may be performed in the absence of a solvent, but is generally carried out in a suitable nonreactive solvent, such as benzene, toluene, xylene, ethylene glycol, pyridine, acetone, phosphorous oxychloride, polyphosphoric acid, and the like, optionally in the presence of a base, such as pyridine or triethylamine, optionally in the presence of a catalytic amount of an acid, such as p-toluenesulfonic acid, or optionally in the presence of a dehydrating agent, such as phosphorous oxychloride, phosphorous pentoxide, or thionyl chloride. Temperatures in the range of −20° C. to 250° C. may be employed with a preferred range of 50°-200° C.

Other similar methods of preparing the compounds are likewise known. Carboxylic acid derivatives of IV may be employed in the above sequence with appropriate modifications in the reaction conditions. For example, an amide derivative of IV may be substituted for the naphthoic acid when condensing with the diamine III, preferably in the presence of a dehydrating agent or base at elevated temperatures, especially in the temperature range of 100°-150° C. If B of Formula IV is cyano, the reaction with the diamine III is typically performed in the presence of a catalytic quantity of an acid, such as p-toluenesulfonic acid, usually at temperatures of 120°-180° C. If B is a thioamide derivative, the condensation with the diamine III is best effected in a solvent, such as ethylene glycol, at temperatures of 100°-150° C. If, in Formula III, A is a halogen, the reaction is performed with the respective amidine derivative of IV. The intermediate thus formed may be first isolated or generated in situ, followed by cyclization at elevated temperatures, preferably in the range of 100°-200° C.

In the preferred scheme above, when the naphthoic acid IV (B is —COOH) is unsubstituted or is substituted with unreactive functionalities (e.q., alkyl, halogen, etc.), heating with the diamine III (A is amino) in polyphosphoric acid (PPA) is the most convenient and preferred method of preparing the respective imidazopyridine. This method was described by Middleton and Wibberley, *J. Het. Chem.*, 17, 1757 (1980), for the preparation of imidazo[4,5-b]- and [4,5-c]pyridines.

When the naphthoic acids of Formula IV are substituted with groups such as alkoxy, PPA treatment can lead to dealkylation and the preferred conditions for the reaction are by refluxing the reactants in phosphorous oxychloride or xylene with the azeotropic removal of water.

Especially when the naphthoic acids (IV) contain phenolic or amino substituents, an alternate method of preparation may be employed. A substituted naphthylaldehyde (IV, B is —CHO) may be treated with sulfur and morpholine to produce the respective substituted-thionaphthoic acid morpholide which on further treatment with methyl iodide gives the S-methyl-substituted-thionaphthoic acid morpholide iodide derivative. Treatment of this intermediate with the appropriate diamine (III, A is amino) in a solvent such as ethylene glycol with heating produces the desired product I (Ia).

The starting materials 2,3- and 3,4-diaminopyridine and 4,5-diaminopyrimidine are commercially available. Other required pyridines of Formula III are either commercially available, or may be prepared in the usual manner from available starting materials by the proper sequence of nitrations, reductions, acylations, hydrolyses, halogenations, and aminations. The required naphthoic acids and derivatives of Formula IV are either commercially available, are known in the literature, or can be prepared by published methods.

In addition, some of the compounds of Formula I (Ia) may be prepared by subsequent derivatizations of other compounds of Formula I (Ia) by methods known in the art. Thus, mercapto derivatives of Formula I (Ia) may be transformed into the respective sulfinyl and sulfonyl compounds, amine derivatives may be prepared from intermediate halo compounds, phenol substituents may be selectively alkylated, and like transformations. The sulfinyl and sulfonyl derivatives of this invention may be prepared directly by the reaction of the corresponding intermediates III with IV, or by oxidation of the corresponding mercapto compounds of Formula I (Ia) by methods known in the art. One or two equivalents, respectively, of hydrogen peroxide in an alcohol, a peracid, such as meta-chloroperbenzoic acid in methylene chloride, or similar oxidants may be used to effect these transformations.

Illustrative of the compounds of this invention are the following:

2-[3-(β-methylsulfinylethoxy)-6-methoxy-2-naphthalenyl]imidazo[4,5-c]pyridine, 2-(1-methoxy-5-methylsulfonyl-2-naphthalenyl)imidazo[4,5-b]pyridine, 8-[1-methoxy-7-(γ-methylmercaptopropoxy)-2-naphthalenyl]purine, 2-[3-methoxy-8-(β-ethylsulfinylethoxy)-2-naphthalenyl]imidazo[4,5-c]pyridine, 2-(3-butoxy-5-methyl-2-naphthalenyl)imidazo[4,5-b]pyridine, 8-[3-(γ-methylsulfinylpropoxy)-2-naphthalenyl]purine, 2-(β-methylsulfinylethoxy)-2-naphthalenyl]imidazo4,5-c]pyridine,
2-(3-methoxy-6-methyl-2-naphthalenyl)imidazo[4,5-b]pyridine,
2-(3-methoxy-5-methylsulfinyl-2-naphthalenyl)imidazo[4,5-c]pyridine,
2-(2-naphthalenyl)imidazo[4,5-b]pyridine,
2-[3-(β-methylmercaptoethoxy)-5-methylmercapto-2-naphthalenyl]imidazo[4,5-b]pyridine,
2-[1-(β-ethylsulfinylethoxy)-8-methoxy-2-naphthalenyl]imidazo[4,5-c]pyridine,
8-(1-methoxy-6-hydroxy-2-naphthalenyl)purine,
2-(4,6-dimethoxy-2-naphthalenyl)imidazo[4,5-b]pyridine,
2-(1,8-dimethoxy-2-naphthalenyl)imidazo[4,5-c]pyridine,
8-(3,5-dimethoxy-2-naphthalenyl)purine,
8-[1-(β-methylsulfinylethoxy)-7-methyl-2-naphthalenyl]purine,
2-[1-methoxy-5-(β-methylmercaptoethoxy)-2-naphthalenyl]imidazo[4,5-c]pyridine,
2-(3,5-dimethoxy-2-naphthalenyl)imidazo[4,5-b]pyridine,
2-(1-fluoro-5-methylsulfinyl-2-naphthalenyl)imidazo[4,5-c]pyridine,
8-(1,5-dimethoxy-2-naphthalenyl)purine,
8-(3-ethoxy-8-propylsulfinyl-2-naphthalenyl)purine,
8-[3-(β-methoxyethoxy)-7-methoxy-2-naphthalenyl]purine,
2-(1-ethoxy-7-ethylsulfonyl-2-naphthalenyl)imidazo[4,5-c]pyridine,
2-(6-isopropoxy-2-naphthalenyl)imidazo[4,5-b]purine,
8-(2-naphthalenyl)purine,
2-(4-β-phenylsulfinylethoxy-6-methoxy-2-naphthalenyl)imidazo[4,5-c]pyridine,
2-[1-(β-methylmercaptoethoxy)-6-methylmercapto-2-naphthalenyl]imidazo[4,5-b]pyridine,
2-(1-methylmercapto-2-naphthalenyl)imidazo[4,5-c]pyridine,
2-[1,6-bis(methylmercapto)-2-naphthalenyl]imidazo[4,5-c]pyridine,
8-(3,6-diethoxy-2-naphthalenyl)purine,
2-[3-(β-ethylmercaptoethoxy)-5-methoxy-2-naphthalenyl]imidazo[4,5-b]pyridine,
2-(1-methoxy-5-propylsulfonyl-2-naphthalenyl)imidazo[4,5-c]pyridine,
2-(4-ethoxy-8-methylsulfinyl-2-naphthalenyl)imidazo[4,5-b]pyridine,
2-(6-amino-2-naphthalenyl)imidazo[4,5-c]pyridine,
2-(3-methoxy-6-propargyloxy-2-naphthalenyl)imidazo[4,5-c]pyridine,
8-(3-ethoxy-7-ethylsulfinyl-2-naphthalenyl)purine
2-(4,5-dimethoxy-2-naphthalenyl)imidazo[4,5-b]pyridine,
8-(3-ethoxy-8-butylsulfinyl-2-naphthalenyl)purine,
2-(4-methoxy-8-methylsulfinyl-2-naphthalenyl)imidazo[4,5-c]pyridine,
2-(3-methoxy-6-hydroxy-2-naphthalenyl)imidazo[4,5-b]pyridine,
2-(1-methoxy-2-naphthalenyl)imidazo[4,5-b]pyridine,
2-(1,6-dichloro-2-naphthalenyl)imidazo[4,5-c]pyridine,
8-(4-ethoxy-8-butylsulfonyl-2-naphthalenyl)purine,
2-[1-β-(4-hydroxyphenylsulfinyl)ethoxy-5-methoxy-2-naphthalenyl]imidazo[4,5-b]pyridine,
2-(1-fluoro-6-methoxy-2-naphthalenyl)imidazo[4,5-c]pyridine,
2-(1-methylamino-2-naphthalenyl)imidazo[4,5-b]pyridine,
2-(6-methylmercapto-2-naphthalenyl)imidazo[4,5-c]pyridine,
2-(1-allyloxy-5-methoxy-2-naphthalenyl)imidazo[4,5-b]pyridine,
8-[4-methoxy-7-(β-ethylmercaptoethoxy)-2-naphthalenyl]purine,
2-(4,5-dimethoxy-2-naphthalenyl)imidazo[4,5-c]pyridine,
8-(8-methoxy-2-naphthalenyl)purine,
8-(1-fluoro-7-methylsulfinyl-2-naphthalenyl)purine,
2-(3-butyl-7-methoxy-2-naphthalenyl)imidazo[4,5-c]pyridine,
2-(4,8-dimethoxy-2-naphthalenyl)imidazo[4,5-b]pyridine,
2-(3-chloro-2-naphthalenyl)imidazo[4,5-c]pyridine,
8-(1-ethoxy-5-butylmercapto-2-naphthalenyl)purine,
2-(3-fluoro-6-methylmercapto-2-naphthalenyl)imidazo[4,5-c]pyridine,
2-(6-hydroxy-2-naphthalenyl)imidazo[4,5-c]pyridine,
2-(4-ethoxy-5-methyl-2-naphthalenyl)imidazo[4,5-b]pyridine,
8-(6-methoxy-2-naphthalenyl)purine,
2-(4-methoxy-2-naphthalenyl)imidazo[4,5-c]pyridine,
8-[1-methoxy-6-(β-methylsulfinylethoxy)-2-naphthalenyl]purine,
2-[1-γ-(3,4-dichlorophenoxy)propoxy-2-naphthalenyl]imidazo[4,5-c]pyridine,
2-[3-(β-methylsulfinylethoxy)-8-methylmercapto-2-naphthalenyl]imidazo[4,5-b]pyridine,
2-(4-methoxy-6-hydroxy-2-naphthalenyl)imidazo[4,5-c]pyridine,
8-(1-hydroxy-6-methoxy-2-naphthalenyl)purine,
8-(4-ethoxy-7-propylmercapto-2-naphthalenyl)purine,
2-(4-fluoro-6-methylsulfonyl-2-naphthalenyl)imidazo[4,5-c]pyridine,
2-(1-methoxy-7-butylmarcapto-2-naphthalenyl)imidazo[4,5-b]pyridine,
8-[4-(γ-ethylsulfinylpropoxy)-6-methoxy-2-naphthalenyl]purine,
8-[1-(β-methylsulfinylethoxy)-5-methylsulfinyl-2-naphthalenyl]purine,
2-(1-methoxy-6-propylsulfinyl-2-naphthalenyl)imidazo[4,5-c]pyridine,
2-(8-methoxy-2-naphthalenyl)imidazo[4,5-b]pyridine,
2-[1-(β-methylmercaptoethoxy)-8-methoxy-2-naphthalenyl]imidazo[4,5-c]pyridine,
8-(4,6-dimethoxy-2-naphthalenyl)purine,
2-(1-methoxy-6-ethoxy-2-naphthalenyl)imidazo[4,5-c]pyridine,
8-(1-methoxy-2-naphthalenyl)purine,
2-(1-methoxy-5-dimethylamino-2-naphthalenyl)imidazo[4,5-b]pyridine,
2-(1-nitro-6-hydroxy-2-naphthalenyl)imidazo[4,5-c]pyridine,
8-(6-cyano-2-naphthalenyl)purine,
2-(7-isopropyl-2-naphthalenyl)imidazo[4,5-c]pyridine,
2-(1-β-phenylethoxy-2-naphthalenyl)imidazo[4,5-b]pyridine,
8-(4,7-dimethoxy-2-naphthalenyl)purine,
2-(1,6-dihydroxy-2-naphthalenyl)imidazo[4,5-c]pyridine,
2-(1-methoxy-6-methylsulfonyl-2-naphthalenyl)imidazo[4,5-c]pyridine,
2-(3-methoxy-6-propylmercapto-2-naphthalenyl)imidazo[4,5-b]pyridine,
8-[1-methoxy-5-(γ-ethylsulfinylpropoxy)-2-naphthalenyl]purine, 2-(1-methoxy-6-chloro-2-naphthalenyl)imidazo[4,5-c]pyridine,
2-[4-(γ-ethylmercaptopropoxy)-7-methoxy-2-naphthalenyl]imidazo[4,5-c]pyridine,
8-(5-methylsulfonyl-2-naphthalenyl)purine,
8-(4-propoxy-5-methyl-2-naphthalenyl)purine,
2-(3-ethoxy-6-methoxy-2-naphthalenyl)imidazo[4,5-b]pyridine,
2-(1-methoxy-6-ethylmercapto-2-naphthalenyl)imidazo[4,5-c]pyridine,
2-(6-methoxy-2-naphthalenyl)imidazo[4,5-b]pyridine,
2-(4-dimethylamino-2-naphthalenyl)imidazo[4,5-b]pyridine,
2-[4-methoxy-7-(γ-ethylmercaptopropoxy)-2-naphthalenyl]imidazo[4,5-c]pyridine,
8-(1,6-dimethyl-2-naphthalenyl)purine,
8-(6-methylsulfinyl-2-naphthalenyl)purine,
2-[3-(β-methylsulfinylethoxy)-5-methylmercapto-2-naphthalenyl]imidazo[4,5-c]pyridine,
2-(3,8-dimethoxy-2-naphthalenyl)imidazo[4,5-b]pyridine,
8-(1-methoxy-6-methylmercapto-2-naphthalenyl)purine,
2-(3,5-dimethoxy-2-naphthalenyl)imidazo[4,5-b]pyridine,
8-(4,5-dimethoxy-2-naphthalenyl)purine,
8-(4-methoxy-7-ethylsulfinyl-2-naphthalenyl)purine,
2-[4-(β-methylsulfinylethoxy)-2-naphthalenyl]imidazo[4,5-c]pyridine,
2-[4-(γ-methylmercaptopropoxy)-6-methoxy-2-naphthalenyl]imidazo[4,5-b]pyridine,
2-(4-iodo-2-naphthalenyl)imidazo[4,5-c]pyridine,
2-[4-methoxy-5-(β-butylsulfinylethoxy)-2-naphthalenyl]imidazo[4,5-c]pyridine,
2-[1-(β-methoxyethoxy)-2-naphthalenyl]imidazo[4,5-c]pyridine,
2-(8-fluoro-2-naphthalenyl)imidazo[4,5-b]pyridine,
2-(7-isopropoxy-2-naphthalenyl)imidazo[4,5-c]pyridine,
8-(3-ethoxy-7-ethylmercapto-2-naphthalenyl)purine,
8-(4-fluoro-5-methoxy-2-naphthalenyl)purine,
8-(1-methoxy-5-methylmercapto-2-naphthalenyl)purine,
2-(1-fluoro-6-methylmercapto-2-naphthalenyl)imidazo[4,5-c]pyridine,
2-[3-methoxy-5-(γ-methylsulfinylpropoxy)-2-naphthalenyl]imidazo[4,5-b]pyridine,
2-(7-methylsulfonyl-2-naphthalenyl)imidazo[4,5-c]pyridine,
8-(5-butoxy-2-naphthalenyl)purine,
8-(4-methylsulfinyl-2-naphthalenyl)purine,
2-(1-methoxy-6-benzyloxy-2-naphthalenyl)imidazo[4,5-c]pyridine.

The pharmaceutically acceptable acid addition salts of this invention include salts derived from inorganic acids such as hydrochloric acid, nitric acid, phosphoric acid, sulfuric acid, hydrobromic acid, hydriodic acid, phosphorous acid and the like, as well as salts derived from nontoxic organic acids such as aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycolate, malate, tartrate, methanesulfonate, propanesulfonate, naphthalene-1-sulfonate, naphthalene-2-sulfonate and the like salts. The preferred salts of this invention are those derived from inorganic acids, especially hydrochloric acid.

The compounds may be administered by various routes including the oral, rectal, transdermal, subcutaneous, intravenous, intramuscular, or intranasal routes, being usually employed in the form of a pharmaceutical composition, although it is a special feature of these compounds that they are effective positive inotropic agents, vasodilators, or bronchodilators following oral administration. Such compositions are prepared in a manner well known in the pharmaceutical art and comprise at least one active compound. Accordingly, the invention includes a pharmaceutical composition comprising as active ingredient a compound of Formula I (Ia) or an acid addition salt thereof, associated with a pharmaceutically acceptable carrier.

In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus the composition can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers are lactose, dextrose, sucrose, sorbitol, mannitol, tarches, gum acacia, calcium phosphate, alginates, tragacanth, gelatin, calcium silicate, microcrystalline cellulose, polyvinylpyrrolidone, cellulose, water, syrup, methyl cellulose, methyl- and propyl-hydroxybenzoates, talc, magnesium stearate or mineral oil. The formulations can additionally include lubricating agents, wetting agents, emulsifying and suspending agents, preserving agents, sweetening agents or flavoring agents. The compositions of the invention may, as is well known in the art, be formulated so as to provide quick, sustained or delayed release of the active ingredient after administration to the patient.

Preferably the compositions are formulated in a unit dosage form, each dosage containing from about 5 to 500 mg., more usually 25 to 300 mg., of the active ingredient. The term "unit dosage form" refers to physically discrete units suitable as unitary dosages for human subjects and other mammals, each unit containing a predetermined quantity of active material calculated to produce the desired therapeutic effect, in association with the required pharmaceutical carrier.

The active compounds are effective over a wide dosage range and for example dosages per day will normally fall within the range of about 0.5 to 300 mg./kg. In the treatment of adult humans, the range of from about 1 to 50 mg./kg., in single or divided doses is preferred. However, it will be understood that the amount of the compound actually administered will be determined by a physician, in the light of the relevant circumstances including the condition to be treated, the choice of compound to be administered, the chosen route of administration, the age, weight, and response of the individual patient, and the severity of the patient's symptoms, and therefore the above dosage ranges are not intended to limit the scope of the invention in any way.

The following preparations and examples further illustrate the preparation of the compounds and formulations of this invention. The examples are illustrative only and are not intended to limit the scope of the invention in any way.

EXAMPLE 1

2-(3,5-Dimethoxy-2-naphthalenyl)imidazo[4,5-c]pyridine

A solution of 4.1 g. of 3,4-diaminopyridine and 8.7 g. of 3,5-dimethoxy-2-naphthoic acid in 250 ml. of phosphorous oxychloride was heated at reflux for 18 hours. The reaction was cooled and evaporated in vacuo. The solid was dissolved in 2N hydrochloric acid, cooled, and adjusted to pH 8. The resulting solid was recovered by filtration and chrom;atographed over silica gel to afford 4.4 g. of the desired title compound, m.p. 178°–180° C.

Analysis: $C_{18}H_{15}N_3O_2$; Calc.: C, 70.81; H, 4.95; N, 13.76; Found: C, 71.07; H, 6.15; N, 11.15.

EXAMPLES 2–5

The following compounds were prepared from 3,4-diaminopyridine and the corresponding naphthoic acid derivative according to the procedure of Example 1. The hydrochloride salts were prepared by crystallization from ethanol/hydrochloric acid. Yields are expressed as percent molar yield.

2. 2-(3-Methoxy-2-naphthalenyl)imidazo[4,5-c]pyridine hydrochloride, m.p. 197°–199° C., 3.5% yield.

Analysis: $C_{17}H_{13}N_3O.HCl$; Calc.: C, 65.49; H, 4.53; N, 13.48; Found: C, 62.75; H, 4.84; N, 12.83.

3. 2-(6-Methoxy-2-naphthalenyl)imidazo[4,5-c]pyridine hydrochloride, m.p. 291°–293° C., 12.3% yield.

Analysis: $C_{17}H_{13}N_3O.HCl$; Calc.: C, 65.49; H, 4.53; N, 13.48; Found: C, 67.24; H, 4.78; N, 13.24.

4. 2-(1-Methoxy-2-naphthalenyl)imidazo[4,5c]pyridine hydrochloride, m.p. 310° C. with decomposition, 32% yield.

Analysis: $C_{17}H_{13}N_3O.HCl$; Calc.: C, 65.49; H, 4.53; N, 13.48; Found: C, 65.16; H, 4.55; N, 13.14.

5. 2-(3,6-Dimethoxy-2-naphthalenyl)imidazo[4,5-c]pyridine hydrochloride, m.p. 234°–236° C., 27% yield.

Analysis: $C_{18}H_{15}N_3O_2.HCl$; Calc.: C, 63.25; H, 4.72; N, 12.29; Cl, 10.37; Found: C, 63.47; H, 4.46; N, 12.04; Cl, 10.57.

EXAMPLES 6–7

The following compounds were prepared from 2-naphthoic acid and the corresponding diamine following the procedure of Example 1 except that polyphosphoric acid (PPA) was used in place of phosphorous oxychloride.

6. 8-(2-Naphthalenyl)purine hydrochloride, m.p. 289°–290° C., 47% yield.

Analysis: $C_{15}H_{10}N_4.HCl$; Calc.: C, 63.72; H, 3.92; N, 19.82; Found: C, 63.51; H, 4.13; N, 19.54.

7. 2-(2-Naphthalenyl)imidazo[4,5-b]pyridine, m.p. 288°–289.5° C., 39% yield.

Analysis: $C_{16}H_{17}N_3$; Calc.: C, 78.35; H, 4.52; N, 17.13; Found: C, 78.11; H, 4.66; N, 16.96.

EXAMPLE 8

2-(2-Naphthalenyl)imidazo[4,5-c]pyridine hydrochloride

The title compound was prepared by the reaction of 3,4-diaminopyridine and 2-naphthoic acid following the general procedure of Example 1 except that a 1:10 mixture of phosphorous pentoxide/methanesulfonic acid was used in place of the phosphorous oxychloride. The hydrochloride salt was formed in the usual way to provide the desired title product, m.p. 300°–301° C., in an 80% molar yield.

Analysis: $C_{16}H_{11}N_3.HCl$; Calc.: C, 68.21; H, 4.29; N, 14.91; Found: C, 68.44; H, 4.35; N, 14.91.

The following formulation examples may employ as active compounds any of the pharmaceutical compounds of the invention.

EXAMPLE 9

Hard gelatin capsules are prepared using the following ingredients:

|  | Quantity (mg./capsule) |
| --- | --- |
| Active compound | 250 |
| Starch dried | 200 |
| Magnesium stearate | 10 |

The above ingredients are mixed and filled into hard gelatin capsules in 460 mg. quantities.

EXAMPLE 10

A tablet formula is prepared using the ingredients below:

|  | Quantity (mg./tablet) |
| --- | --- |
| Active compound | 250 |
| Cellulose, microcrystalline | 400 |
| Silicon dioxide, fumed | 10 |
| Stearic acid | 5 |

The components are blended and compressed to form tablets each weighing 665 mg.

EXAMPLE 11

An aerosol solution is prepared containing the following components:

|  | Weight % |
| --- | --- |
| Active ingredient | 0.25 |
| Ethanol | 29.75 |
| Propellant 22 (Chlorodifluoromethane) | 70 |

The active compound is mixed with ethanol and the mixture added to a portion of the propellant 22, cooled to −30° C. and transferred to a filling device. The required amount is then fed to a stainless steel container and diluted with the remaining amount of propellant. The valve units are then fitted to the container.

EXAMPLE 12

Tablets each containing 60 mg. of active ingredient are made up as follows:

| | |
|---|---|
| Active ingredient | 60 mg. |
| Starch | 45 mg. |
| Microcrystalline cellulose | 35 mg. |
| Polyvinylpyrrolidone | 4 mg. |
| (as 10% solution in water) | |
| Sodium carboxymethyl starch | 4.5 mg. |
| Magnesium stearate | 0.5 mg. |
| Talc | 1 mg. |
| Total | 150 mg. |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate and talc, previously passed through a No. 60 mesh U.S. sieve, are then added to the granules which, after mixing are compressed on a tablet machine to yield tablets each weighting 150 mg.

EXAMPLE 13

Capsules each containing 80 mg of medicament are made as follows:

| | |
|---|---|
| Active ingredient | 80 mg. |
| Starch | 59 mg. |
| Microcrystalline cellulose | 59 mg. |
| Magnesium stearate | 2 mg. |
| Total | 200 mg. |

The active ingredient, cellulose, starch and magnesium stearate are blended, passed through a No. 45 mesh U.S. sieve, and filled into hard gelatin capsules in 200 mg. quantities.

EXAMPLE 14

Suppositories each containing 225 mg. of active ingredient are made as follows:

| | |
|---|---|
| Active ingredient | 225 mg. |
| Saturated fatty acid glycerides to | 2,000 mg. |

The active ingredient is passed through a No. 60 mesh U.S. sieve and suspended in the saturated fatty acid glycerides previously melted using the minimum heat necessary. The mixture is then poured into a suppository mold of nominal 2 g. capacity and allowed to cool.

EXAMPLE 15

Suspensions each containing 50 mg. of medicament per 5 ml. dose are made as follows:

| | |
|---|---|
| Active ingredient | 50 mg. |
| Sodium carboxymethyl cellulose | 50 mg. |
| Syrup | 1.25 ml. |
| Benzoic acid solution | 0.10 ml. |
| Flavor | q.v |
| Color | q.v |
| Purified water to | 5 ml. |

The medicament is passed through a No. 45 mesh U.S. sieve and mixed with the sodium carboxymethylcellulose and syrup to form a smooth paste. The benzoic acid solution, flavor and color are diluted with some of the water and added, with stirring. Sufficient water is then added to produce the required volume.

The compounds of this invention and their pharmaceutically acceptable salts have been found to possess useful pharmaceutical properties, including positive inotropy, vasodilation, and anticoagulation. In addition, the compounds have phosphodiesterase inhibition activity and are active in the Herxheimer assay, suggesting their use as compounds effective in treating or preventing bronchial asthma, chronic obstructive pulmonary disease, infant apnea, and related disorders. Furthermore, certain of the compounds of this invention, especially the 2-(2-naphthalenyl)imidazo[4,5-b]pyridines, have demonstrated herbicidal activity against such vegetation as tomatoes, pigweed, and crabgrass. Certain compounds of the present invention were examined as to their pharmacodynamic effects in the following test systems.

Positive Inotropic Activity in Isolated Cat Papillary Muscles

Cats of either sex were anesthetized with Metofane (1,1-difluoro-2,2-dichloroethyl methyl ether, Pittman-Moore) their hearts immediately removed and the papillary muscles dissected and suspended in individual organ baths. A platinum hook secured one end of the muscle to an electrode mounted in the bottom of the bath, and a silk thread attached the tendon to a Statham isometric transducer. The baths contained Krebs-Henseleit solution (36° C., bubbled with 95 percent oxygen-5 percent carbon dioxide) of the following millimolar composition: NaCl, 118; KCl, 4.5; $CaCl_2$, 2.5; $KH_2PO_4$, 1.1; $MgSO_4$, 1.2; $NaHCO_3$, 25; and glucose, 11.

A base-line tension of 1.5 g. was applied to each muscle. Square-wave pulses (5.0 msec. in duration, 20 percent above threshold voltage) delivered through the hook electrode and a second electrode positioned near the top of the muscle evoked 12 contractions/minute, which were recorded on a Grass polygraph. After the muscles were equilibrated for 60 minutes, drugs were introduced in normal saline to bring the final concentration of the drug to $10^{-5}$ or $10^{-4}$ molar. Increases in contractility were tabulated as millimeters of pen deflection in excess of the baseline values. In each experiment the maximum contractility was measured. Test results are summarized in Table I and are expressed as percent of control (control=100 percent) Values are the average of results from 2 to 8 muscles.

TABLE I

Effects of Compounds of Formula I (Ia) on Contractility in Cat Papillary Muscles

| Compound of Example No. | Contractility of Papillary Muscle* Drug Concentration | |
|---|---|---|
| | $10^{-5}M$ | $10^{-4}M$ |
| 1 | 106 | 94 |
| 2 | 117 | 152 |
| 3 | 174 | 224 |
| 4 | 82 | 203 |
| 5 | 110 | 129 |

TABLE I-continued
Effects of Compounds of Formula I (Ia) on Contractility in Cat Papillary Muscles

| Compound of Example No. | Contractility of Papillary Muscle* Drug Concentration | |
|---|---|---|
| | $10^{-5}M$ | $10^{-4}M$ |
| 6 | 110 | 126 |
| 7 | 96 | 147 |
| 8 | 144 | 319 |

*Data are peak responses at the indicated concentration of drug and are expressed as a percent of control (control = 100 percent).

Experiments in Anesthetized Dogs

Mongrel dogs of either sex ranging in weight from 7 to 14 kg. were used. Anesthesia was induced with sodium pentobarbital (30 mg./kg., i.v.) and maintained with supplemental doses as required. A positive-pressure pump was used to ventilate the dogs through an endotracheal tube (18 strokes/minute, 20 ml./kg. stroke$^{-1}$), and a heating pad kept the body temperature at 37°–38° C.

Femoral arterial blood pressure was measured through a polyethylene catheter filled with heparin solution (16 units/ml.) and connected to a Statham pressure transducer. A strain-gauge arch sutured to the right ventricle of the heart measured cardiac contractility. Tension on the gauge was adjusted to 50 g. and the gain of the recorder (Beckman dynograph) was set so that 50 g. caused a 10-mm. pen deflection; cardiac contractile tension was measured as millimeters of pen deflection or grams of tension. The drug was administered following a 30–45 minute equilibrium period as an i.v. bolus (2–5 ml.) in a normal saline vehicle. In a control experiment, rapid intravenous injection of 50 ml. of 5 percent dextran and mechanical compression of the aorta showed that the contractility measurements were independent of changes in preload and afterload. Heart rate was derived by means of a cardiotach which was triggered by the arterial pressure pulse signal and displayed on the polygraph. The maximum effects on contractility at various dose levels are presented as a percent of control (control = 100 percent) in Table II.

TABLE II
Effects of Compounds I (Ia) on Ventricular Contractility in the Anesthetized Dog Effect on Contractility*

| Compound of Example No. | Drug Dose | | | |
|---|---|---|---|---|
| | 1 mg./kg. | 2 mg./kg. | 4 mg./kg. | 8 mg./kg. |
| 3 | 120 | 125 | 155 | 240 |
| 8 | 146 | 170 | 208 | 235 |

*Data are peak responses to an i.v. injection of drug and expressed as a percent of control (control = 100 percent).

I claim:

1. A compound of the formulas

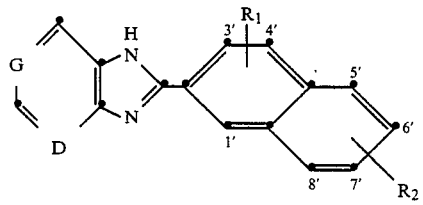

and

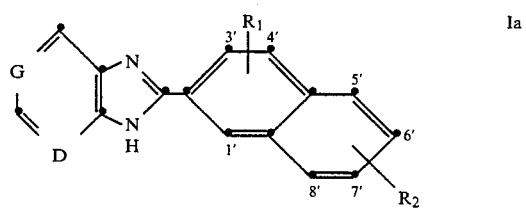

and their pharmaceutically acceptable salts, wherein:
each of $R_1$ and $R_2$ is independently hydrogen, $C_1-C_4$ alkyl, $C_1-C_4$ alkoxy, allyloxy, propargyloxy, benzyloxy, ($C_1-C_4$ alkyl)thio, ($C_1-C_4$ alkyl)sulfinyl, ($C_1-C_4$ alkyl)sulfonyl, hydroxy, halo, cyano, nitro, amino, mono- or di-($C_1-C_4$ alkyl)amino, trifluoromethyl or Z-Q-substituted $C_1-C_4$ alkoxy, wherein Q is oxygen, sulfur, sulfinyl, sulfonyl, or a bond, and Z is $C_1-C_4$ alkyl, phenyl or phenyl substituted with halo, $C_1-C_4$ alkyl, $C_1-C_4$ alkoxy, hydroxy, nitro, amino, ($C_1-C_4$ alkyl)thio, ($C_1-C_4$ alkyl)sulfinyl, or ($C_1-C_4$ alkyl)sulfonyl; and
G and D are each independently N or CH with the proviso that G and D may not both be CH at the same time.

2. A compound of claim 1 wherein $R_1$ is hydrogen.
3. A compound of claim 1 wherein $R_1$ is $C_1-C_4$ alkoxy.
4. A compound of claim 3 wherein $R_1$ is methoxy.
5. A compound of claim 1 wherein $R_2$ is hydrogen.
6. A compound of claim 1 wherein $R_2$ is $C_1-C_4$ alkoxy.
7. A compound of claim 6 wherein $R_2$ is methoxy.
8. A compound of claim 1 wherein G is N and D is CH.
9. The compound of claim 7 which is 2-(6-methoxy-2-naphthalenyl)imidazo[4,5-c]pyridine or a pharmaceutically acceptable salt thereof.
10. The compound of claim 4 which is 2-(1-methoxy-2-naphthalenyl)imidazo[4,5-c]pyridine or a pharmaceutically acceptable salt thereof.
11. The compound of claim 8 which is 2-(2-naphthalenyl)imidazo[4,5-c]pyridine or a pharmaceutically acceptable salt thereof.
12. A method of producing a positive inotropic effect, delaying coagulation of the blood, causing bronchodilation, or causing vasodilation in a warm-blooded mammal, which comprises administering to said mammal an effective amount of a compound of claim 1.
13. The method of claim 12 wherein $R_1$ is methoxy.
14. The method of claim 12 wherein $R_2$ is methoxy.
15. The method of claim 12 wherein G is N and D is CH.
16. A pharmaceutical composition useful to produce a positive in otropic effect, delaying coagulation of the blood, causing bronchodilation, or causing vasodilation in a warm-blooded mammal which comprises an effective amount of a compound of claim 1 and a pharmaceutically acceptable carrier or diluent.
17. A composition of claim 16 wherein $R_1$ is methoxy.
18. A composition of claim 16 wherein $R_2$ is methoxy.
19. A composition of claim 16 wherein G is N and D is CH.
20. A composition of claim 16 which is formulated for oral administration.

* * * * *